(12) United States Patent
Bartyczak et al.

(10) Patent No.: US 10,429,258 B1
(45) Date of Patent: Oct. 1, 2019

(54) BLAST ATTENUATION MOUNT

(71) Applicants: Susan L. Bartyczak, King George, VA (US); Willis Mock, Jr., Fredericksburg, VA (US); Lauren N. Edgerton, Milford, VA (US)

(72) Inventors: Susan L. Bartyczak, King George, VA (US); Willis Mock, Jr., Fredericksburg, VA (US); Lauren N. Edgerton, Milford, VA (US)

(73) Assignee: United States of America, as represented by the Secretary of the Navy, Arlington, VA (US)

( * ) Notice: Subject to any disclaimer, the term of this patent is extended or adjusted under 35 U.S.C. 154(b) by 194 days.

(21) Appl. No.: 15/701,774

(22) Filed: Sep. 12, 2017

Related U.S. Application Data

(60) Provisional application No. 62/520,625, filed on Jun. 16, 2017.

(51) Int. Cl.
*G01L 7/00* (2006.01)
*G01L 7/04* (2006.01)
(Continued)

(52) U.S. Cl.
CPC .............. *G01L 7/043* (2013.01); *F41A 21/08* (2013.01); *G01L 1/2218* (2013.01); *G01P 3/665* (2013.01); *G01N 2203/0066* (2013.01)

(58) Field of Classification Search
CPC ........ G01L 7/043; G01L 1/2218; F41A 21/08; G01P 3/665; G01N 2203/0066
See application file for complete search history.

(56) References Cited

U.S. PATENT DOCUMENTS

| 4,114,510 A | 9/1978 | Prince et al. ..................... 89/12 |
| 6,250,198 B1 | 6/2001 | Vendetti et al. ............. 89/44.02 |

(Continued)

OTHER PUBLICATIONS

S. L., Bartyczak et al.: "Versatile gas gun target assembly for studying ballast wave mitigation in materials", AIP Conf. Proc. 1426, 501 (2012).

(Continued)

*Primary Examiner* — Freddie Kirkland, III
(74) *Attorney, Agent, or Firm* — Gerhard W. Thielman

(57) ABSTRACT

A test fixture is provided for evaluating structural response of a sample to blast pressure from a muzzle of a gas gun. The fixture includes an adapter, an annular flange, a gauge assembly and a target assembly. The adapter has a proximal rim and an expansion tube. The rim attaches to the muzzle to direct the blast pressure into the tube towards an exit opposite the rim. The annular flange has a ring and a shim that attaches to the tube at the exit. The gauge assembly contains the sample between upstream and downstream stress gauges. The target assembly contains the gauge assembly. The target assembly includes front and rear annular plates connecting coaxially in parallel. The rear annular plate connects to the ring. The tube carries the blast pressure through the exit to strike the gauge assembly for the stress gauges to measure stress from the blast pressure. The ring includes first circumferentially distributed through-holes substantially parallel to the flange's symmetry axis and second circumferentially distributed mutually parallel through-holes angularly offset from the symmetry axis for mounting the rear plate to the ring either coaxially or at an oblique angle.

12 Claims, 5 Drawing Sheets

(51) Int. Cl.
*G01P 3/66* (2006.01)
*F41A 21/08* (2006.01)
*G01L 1/22* (2006.01)

(56) References Cited

U.S. PATENT DOCUMENTS

| | | | | |
|---|---|---|---|---|
| 7,825,850 B2* | 11/2010 | Frick | ............. | F41A 21/32 |
| | | | | 342/115 |
| 8,776,606 B2* | 7/2014 | Slocum | ............. | G01L 7/043 |
| | | | | 604/227 |
| 8,935,963 B2 | 1/2015 | Bartyczak et al. | ............. | 73/750 |
| 2014/0026669 A1* | 1/2014 | Bartyczak | ............. | G01L 7/00 |
| | | | | 73/756 |

OTHER PUBLICATIONS

PCB Piezotronics Model 132A31 Installation and Operating Manual http://www.pcb.com/contentstore/docs/PCB_Corporate/Pressure/Products/Manuals/132A31.pdf.

\* cited by examiner

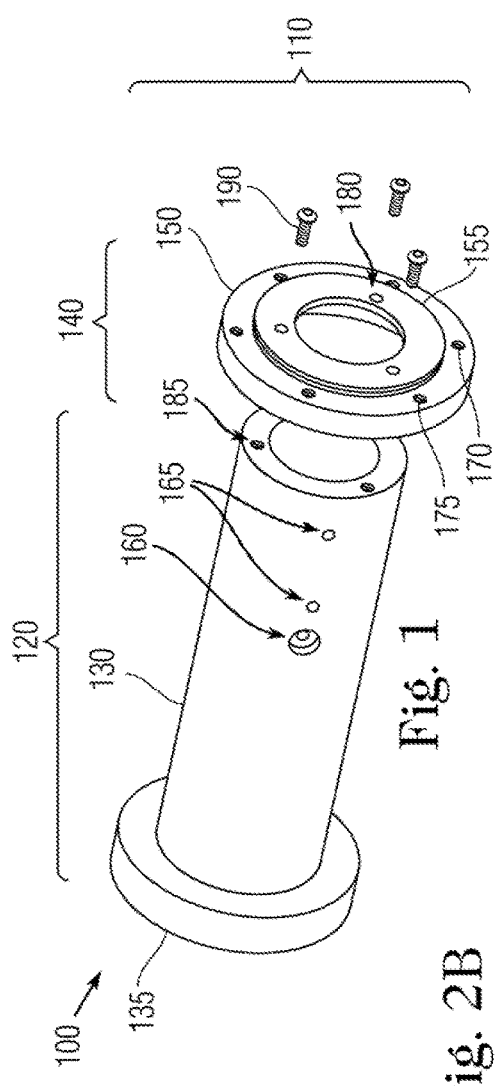
Fig. 1
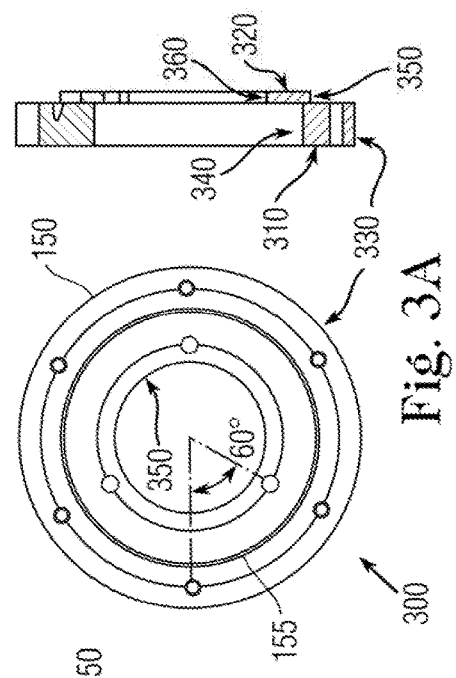
Fig. 3A
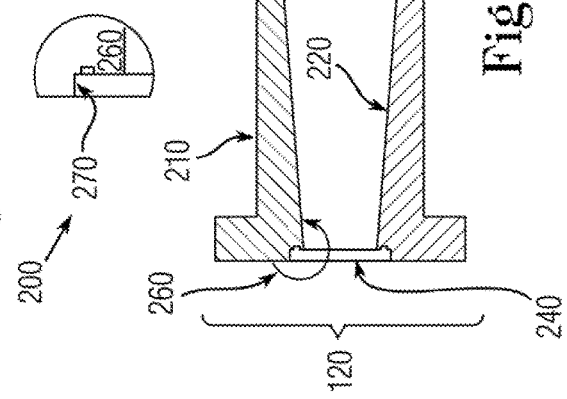
Fig. 2A
Fig. 2B

BLAST ATTENUATION MOUNT

CROSS REFERENCE TO RELATED APPLICATION

Pursuant to 35 U.S.C. § 119, the benefit of priority from provisional application 62/520,625, with a filing date of Jun. 16, 2017, is claimed for this non-provisional application.

STATEMENT OF GOVERNMENT INTEREST

The invention described was made in the performance of official duties by one or more employees of the Department of the Navy, and thus, the invention herein may be manufactured, used or licensed by or for the Government of the United States of America for governmental purposes without the payment of any royalties thereon or therefor.

BACKGROUND

The invention relates generally to a mounting apparatus for studying blast attenuation of layered panels from gas gun exposure. In particular, the invention provides a gas gun interface mount to enable response testing at normal and oblique incidence angles of layered panels.

Conventional methods of measuring blast wave propagation through materials have involved the use of small explosive charges or a gas gun equipped with a Mylar burst diaphragm to generate the blast wave and complex target geometries such as instrumented mannequin heads wearing helmets coated with different test materials. There are three key disadvantages to these techniques:
(1) explosive charges pose safety and environmental hazards,
(2) the repeatability of Mylar burst diaphragms is poor at low pressures (below 100 psi), and
(3) complex target geometries introduce uncertainties in the data due to irregular flow of the blast wave around targets and into the interfaces between the helmets and the instrumented mannequin heads.

U.S. Pat. No. 8,935,963 (issued Jan. 20, 2015) addresses these disadvantages by adapting a simplified target geometry to an existing gas gun equipped with a fast-opening valve. Even though that reference describes a much improved method compared to traditional methods for low pressure blast wave measurements, several limitations remain. These include:
(1) test material blast area diameters are limited to only 2.5" (inches), which in turn limits the thickness of the materials to be tested due to edge release waves interfering with the longitudinal blast wave;
(2) the impact surface of the test materials can be positioned only normal to the blast wave, which precludes the important non-normal blast region from being investigated; and
(3) because the target materials are located inside a tight-fitting polymethyl methacrylate (PMMA) tube for testing, fragile target strain gauge leads must be carefully threaded in a restrictive PMMA slot to exit the target assembly for attaching to measurement instrumentation.

SUMMARY

Conventional blast test fixtures yield disadvantages addressed by various exemplary embodiments of the present invention. In particular, various exemplary embodiments provide a test fixture for evaluating structural response of a sample to blast pressure from a muzzle of a gas gun. The fixture includes an adapter, an annular flange, a gauge assembly and a target assembly. The adapter has a proximal rim and an expansion tube. The rim attaches to the muzzle to direct the blast pressure into the tube towards an exit opposite the rim. The annular flange has a ring and a shim that attaches to the tube at the exit.

In exemplary embodiments, the gauge assembly contains the sample between upstream and downstream stress gauges. The target assembly contains the gauge assembly. The target assembly includes front and rear annular plates connecting coaxially in parallel. The rear annular plate connects to the ring. The tube carries the blast pressure through the exit to strike the gauge assembly for the stress gauges to measure stress from the blast pressure. The ring includes first circumferentially distributed through-holes substantially parallel to the flange's symmetry axis and second circumferentially distributed mutually parallel through-holes angularly offset from the symmetry axis for mounting the rear plate to the ring either coaxially or at an oblique angle.

BRIEF DESCRIPTION OF THE DRAWINGS

These and various other features and aspects of various exemplary embodiments will be readily understood with reference to the following detailed description taken in conjunction with the accompanying drawings, in which like or similar numbers are used throughout, and in which:

FIG. 1 is an isometric exploded view of a muzzle adapter assembly;

FIG. 2A is an elevation cross-section view of a muzzle adapter;

FIG. 2B is a detail view of an O-ring groove for a fixed muzzle adapter flange;

FIG. 3A is a set of elevation views of the flange;

DETAILED DESCRIPTION

Figure 3C:
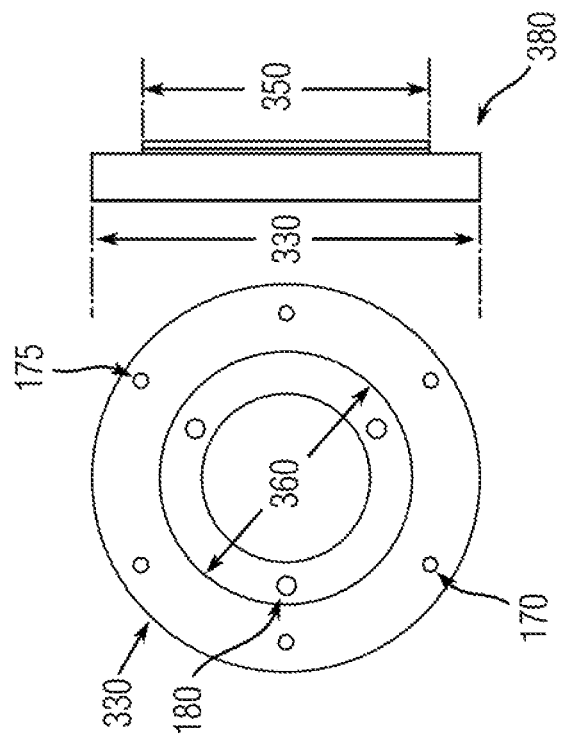
FIG. 3C is a set of elevation views of the flange.

In the following detailed description of exemplary embodiments of the invention, reference is made to the accompanying drawings that form a part hereof, and in which is shown by way of illustration specific exemplary embodiments in which the invention may be practiced. These embodiments are described in sufficient detail to enable those skilled in the art to practice the invention. Other embodiments may be utilized, and logical, mechanical, and other changes may be made without departing from the spirit or scope of the present invention. The following detailed description is, therefore, not to be taken in a limiting sense, and the scope of the present invention is defined only by the appended claims.

The purpose of the exemplary embodiments is to provide a simpler and more versatile capability, compared to present technology, for measuring blast attenuation properties of layered panels subjected to normal and non-normal planar blast wave impact from a gas gun.

Five important advantages of exemplary embodiments over U.S. Pat. No. 8,935,963 include:

(1) a design that adapts to an existing gas gun that uses a fast-opening valve and non-explosive nitrogen and helium gases to generate the blast wave thereby eliminating the safety and environmental hazards associated with explosive charges and the poor repeatability issues associated with Mylar burst diaphragms;

(2) a 2.5" (inches) bore muzzle adapter compared to 4.25" previously, thereby obtaining the same blast pressure by using less helium gas, which is in short supply worldwide;

(3) a test material blast area diameter of 3.0" compared to 2.5" previously, resulting in a 47% increase in blast area which in turn enables thicker materials to be tested due to a later arrival of edge release waves at the target center;

(4) a simpler target assembly design compared to previously that enables blast attenuation for any target diameter and thickness to be measured; and (5) the capability to select any angle between the impact surface of the test material and the blast wave; for exemplary embodiments the standard normal impact and the important 15° (degrees) from normal impact were selected for the experiments.

Due to recent military conflicts, especially in the Middle East, more blast-related head injuries have been detected and diagnosed, i.e., traumatic brain injury (TBI). For this reason, there has been a renewed interest in developing blast mitigating materials for helmets and other structures. Exemplary embodiments have the potential to be used commercially by other facilities using gas guns to characterize blast wave attenuation of the new materials they develop. The exemplary apparatus provides an improved, simplified, and fast turn-around-time capability for measuring blast attenuation properties of layered panels subjected to planar blast wave impact from a gas gun at normal or angle incidence with the objective of identifying materials suitable for military armor to protect warfighters from blast-related injuries.

FIG. 1 shows an exploded isometric view 100 of a muzzle adapter assembly 110. A muzzle adapter 120 that comprises an expansion tube 130 and a radially extending proximal rim 135 that attaches to a gun muzzle. A removable annular flange 140 includes a proximal ring 150 and a distal shim 155. An instrumentation recess 160 and two pressure taps 165 are longitudinally disposed along the adapter 120. Straight and slanted through-holes 170 and 175 are circumferentially disposed through the thickness of the ring 150. Through-holes 180 are aligned with the slanted holes 175 and circumferentially disposed on the shim 155. Corresponding bore holes 185 parallel to the bore axis at the distal end of the tube 130 align with the through-holes 180. Screws 190 can be inserted through the aligned holes 180 and 185 to securely attach the flange 140 to the muzzle of the adapter 120.

FIG. 2A shows a cross-section view 200 of the muzzle adapter 120. The expansion tube 130 has a straight outer profile 210 of uniform diameter. The inner surface includes a proximal expanding profile 220 and a distal straight profile 230. An entrance 240 at the rim 135 has a slightly larger diameter than the entrance of the expanding profile 220. The distal muzzle of the expansion tube 130 corresponds to an exit 250. FIG. 2B shows the detail view 260 of the entrance shape at a recess 270 along the inner surface 220.

Figure 3B:
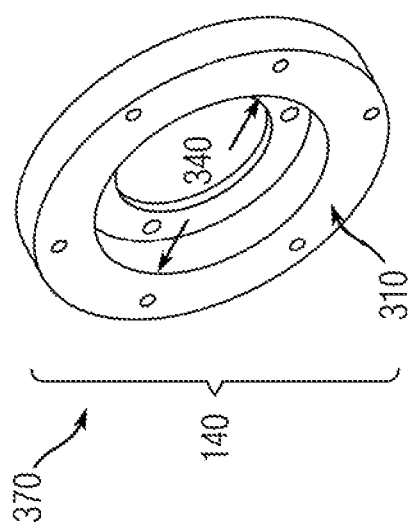
FIG. 3B is an isometric view of the flange.

FIG. 3A shows front and cross-section elevation views 300 of the flange 140, including the ring 150 and the shim 155. The ring 150 has a proximal face 310 that abuts the muzzle end of the tube 130, while the shim 155 has a distal face 320. The ring 150 has an outer circular rim 330 that corresponds to an outer diameter (o.d.) and an inner circular annulus 340 that corresponds to an inner diameter (i.d.). The shim 155 has an outer circular rim 350 that corresponds to an o.d., and an inner circular annulus 360 that corresponds to an i.d. FIG. 3B shows an isometric view 370 of the flange 140. FIG. 3C shows rear and edge elevation views 380 of the flange 140. The target assembly attaches to the flange 140 with three threaded rods described subsequently.

These components—the adapter 120 and the flange 140—are fabricated from 6061-T6 aluminum alloy. The muzzle adapter 120 is 12.0" (inches) long. The non-removable rim 135 is 1.0" wide with a 5.50" Ø o.d. The tube 130 along the outer profile 210 is 3.75" Ø o.d. for the remaining 11.0" along the longitudinal axis. The gun barrel inserts into the recess (2.2" Ø diameter×0.25" deep) of the rim 135. The recess 270 (shown in detail view 260) has an O-ring groove (1.78" Ø i.d. and 2.06" Ø o.d.×0.08" deep) that contains a Parker 2-134 O-ring that seals the junction between the barrel and the rim 135 for blast pressure. The rim 135 includes three ½-13 UNC threaded holes spaced 120° apart on a 4.25" Ø diameter bolt circle for securing the muzzle adapter 120 to the gun barrel.

The muzzle adapter 120 has a 5.75" long transition region with increasing inside diameter along the inner proximal profile 220 to study materials with a diameter larger than the 1.575" Ø gun bore diameter. A larger target diameter enables one-dimensional strain conditions in the target center for a longer time before release waves from the target edge reach the center.

In this transition region shown by profile 220, the inside diameter of the muzzle adapter 120 on the gun barrel end increases from 1.63" Ø to 2.5" Ø. This expansion corresponds to a 4.8° angle. The 2.5" Ø i.d. for the inner distal profile 230 is continued (for a distance of 6.0") to the target assembly end of the muzzle adapter 120 at the exit 250. This end of the muzzle adapter has three ¼-28 UNF threaded holes spaced 120° apart on a 3.125" Ø diameter bolt circle for securing the muzzle adapter to the removable adapter flange 140.

The muzzle adapter 120 contains three pressure gauges: a 132A31 pressure sensor gauge from PCB Piezoelectronics™ from Depew, N.Y. at the recess 160 for triggering the recording oscilloscopes and two PCB 113A31 gauges (PG1 and PG2) at the taps 165 for measuring the blast wave velocity and pressure. These gauges are respectively located 4.0", 3.0", and 1.0" from upstream the target assembly end at the exit 250. Standard PCB mounting techniques are used to secure the pressure gauges to the muzzle adapter 120 along the tube 130.

The removable annular flange 140 is 0.875" wide with a 5.75" Ø o.d. for the rim 330 and fabricated from 6061-T6 aluminum alloy. The 3.75" o.d. muzzle adapter 120 fits in a 3.78" Ø diameter×0.70" deep recess in the ring 150. The annular shim 155 is secured with three ¼-28 button hex head bolts 190 that fit in three 0.28" Ø thru holes 180 on a 3.125" Ø bolt circle and into the bore holes 185 of the tube 130. The bolts 190 rest on a 0.125" thick×4.25" Ø inch diameter step. The flange 140 on the shim 155 has the same 2.5" Ø i.d. for the rim 360 as the muzzle adapter 120 along the distal profile 230. These holes 170 and 180 are parallel to the axi-symmetric annulus of the flange 140. By contrast, the slant holes 175 are angularly offset from this symmetry axis.

Figure 4:
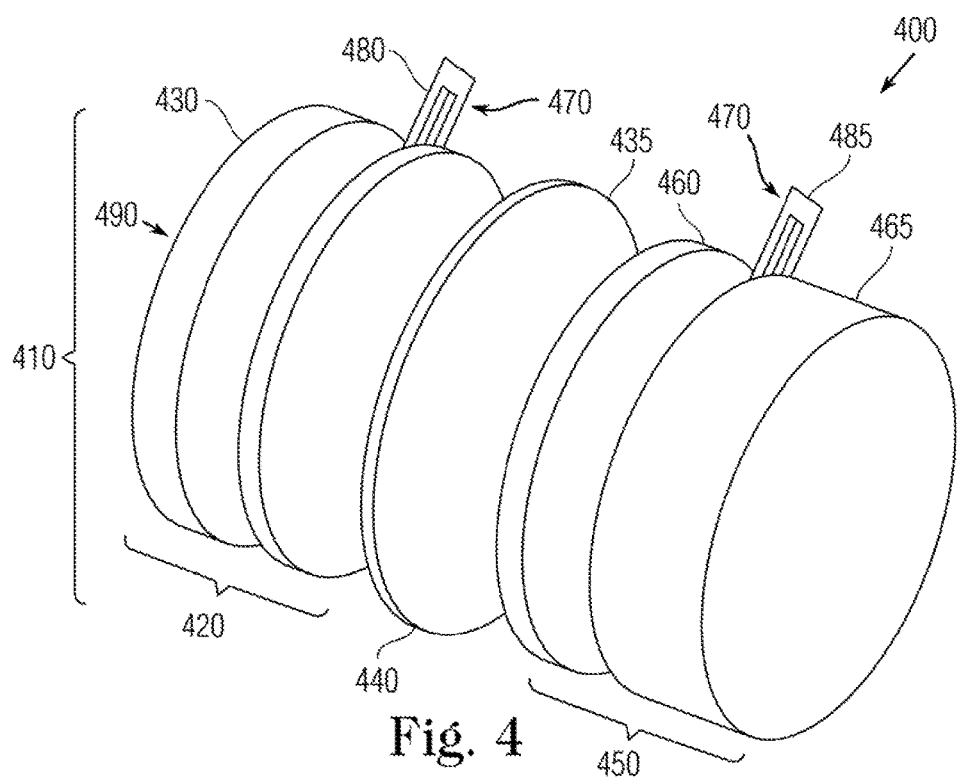
FIG. 4 is an isometric assembly view of a gauge assembly.

FIG. 4 shows an exploded isometric view 400 of a gauge assembly 410 with a target sample sandwiched between proximal and distal gauge packages. The proximal (windward) gauge package 420 includes a first disk 430 and a second disk 435. The test sample 440 constitutes a target material to be subjected to the gun blast. The distal (leeward)

gauge package 450 includes a third disk 460 and a fourth disk 465. These disks 430, 435, 460 and 465 are composed of 6061-T6 aluminum alloy. A corresponding pair 470 of polyvinylidene fluoride (PVDF) stress gauges 480 and 485 extends radially outward within the gauge packages 420 and 450. The upstream stress gauge PVDF1 480 is disposed between the disks 430 and 435 ahead of the sample 440. The downstream stress gauge PVDF2 485 is disposed between and disks 460 and 465 behind the sample 440.

The sample 440 is disposed between the proximal and distal gauge packages 420 and 450, each of which contains one of the pair 470 of stress gauges sandwiched between two 3.25" Ø diameter aluminum disks. The proximal gauge package 420 comprises the upstream stress gauge PVDF1 480 sandwiched between one 0.37" thick aluminum disk 430 on the impact (or wind) side and one 0.25" thick aluminum disk 435 on the lee side that interfaces with the obverse of the sample 440. The distal gauge package 450 comprises the downstream stress gauge PVDF2 485 sandwiched between one 0.25" thick aluminum disk 460 on the front side that interfaces with the reverse of the sample 440 and one 1.0" thick aluminum disk 465 on the lee side. Arrow 490 denotes blast wave forces from the gun.

Figure 5:
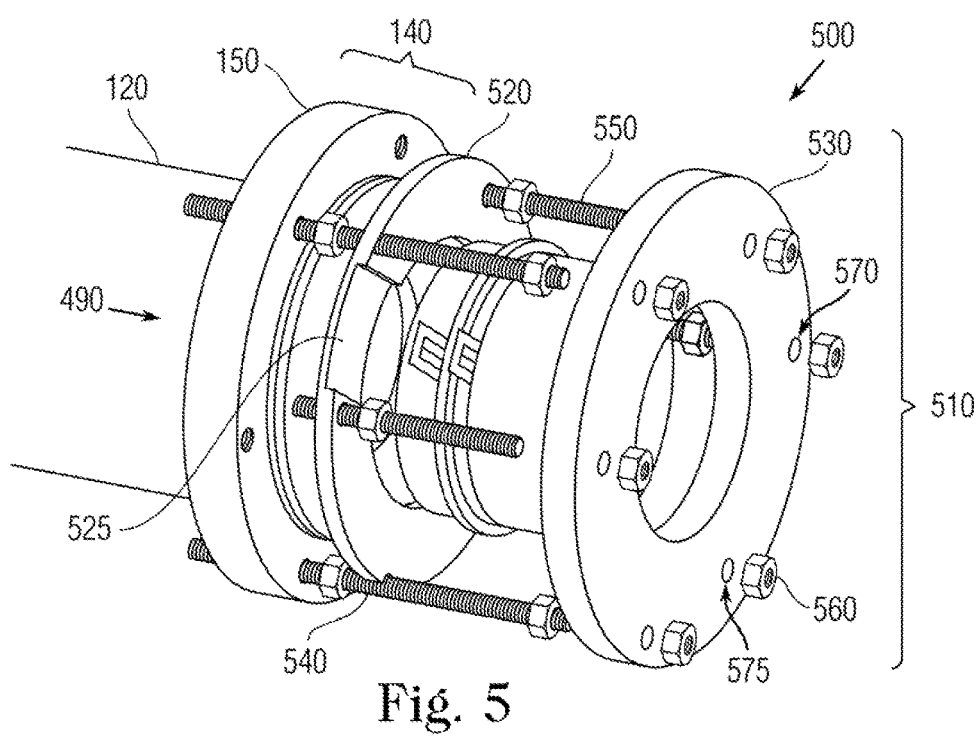
FIG. 5 is an isometric exploded view of a target assembly.

FIG. 5 shows an exploded isometric view 500 of a target assembly 510 attached to flange 140. The target assembly 510 includes a front annular plate 520 with a recess 525, the gauge assembly 410, and a rear annular plate 530. Recall that the gauge assembly 410 includes proximal and distal gauge packages 420 and 450 that sandwich the sample 440 as the target.

The rear plate 530 is secured to the flange 140 by long threaded rods 540. The plates 520 and 530 are secured to each other by short threaded rods 550. Hex nuts 560 secure both rods 540 and 550 where they protrude through the holes 570 and 575 on the rear plate 530. The gun blast imparts the blast wave forces by arrow 490 pushing the flange 140 in tension from the adapter 120.

Figure 6:
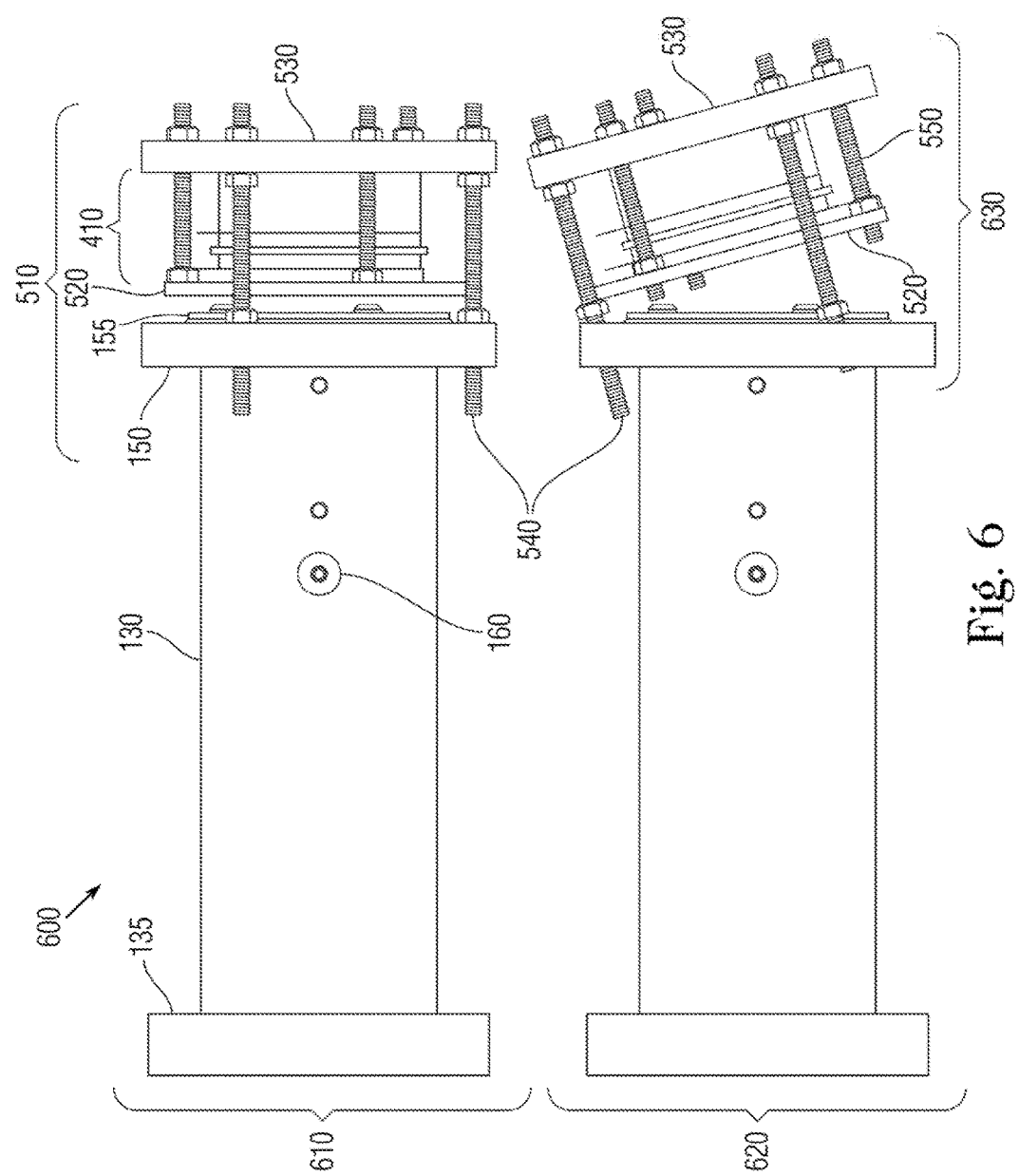
FIG. 6 is a planar view of the target assembly in two configurations.

FIG. 6 shows an assembly elevation view 600 of the position of the two target orientations for exemplary embodiments. A first configuration 610 for normal orientation imposes 90° impact of the blast wave 580 on the sample 440 within the gauge assembly 410. A second configuration 620 for oblique orientation imposes 75° impact of the blast wave 580 on the sample 440.

For a right angle (90° blast wave impact experiment, the face of the target assembly 510 is offset from the three button head bolts 190 by approximately 0.25". This gap enables blast gas overpressure to escape after the experimental data have been recorded. For a non-normal 75° blast wave impact experiment, the blast overpressure relieves due to the 15° tilt of the face of the target assembly 630 to the flange 140.

The first configuration 610 depicts the tube 130 of the adapter 120 with the rim 135 at the gun muzzle attached to the ring 150 of the flange 140. For this normal impact version, the rear plate 530 attaches to the flange 140 via the long rods 540 passing through the straight through-holes 170 and 570 aligned together. The front plate 520 attaches to the rear plate 530 coaxially and in parallel via the short rods 550 with the gauge assembly 410 containing the sample 440 sandwiched between the gauge packages 420 and 450.

In the second configuration 620, the rear plate 530 attaches to the flange 140 via the long rods 540 passing through the slanted through-holes 175 and straight through-holes 570 aligned together, providing a target assembly 610 canted at an angle of 15° from normal to the blast wave 580, to thereby empirically evaluate oblique blast effects on the sample 440. Thus, for the oblique configuration, the front and rear plates 520 and 530 are parallel and coaxial to each other, but canted to the flange 140. Artisans of ordinary skill will recognize that the angle of 15° is exemplary for conditions tested and not inherently limiting.

The normal target assembly 510 has three ¼-28 thru holes 170 on a 5.0" diameter bolt circle that attaches to the flange 140 with three ¼-28 threaded rods 540 that are 5.0" long. This is also applicable to the oblique target assembly 630. Any angle can therefore be selected between the test face of the sample 440 and the blast wave by drilling three holes 175 in the flange 140 in the ring 150 for the selected orientation. For exemplary embodiments, two orientations were chosen for experimentation, the standard normal impact assembly 510 and the important 15° oblique impact assembly 630.

For normal impact (i.e., blast wave impacts the target face at 90°) three equally spaced ¼-28 through holes 170 were drilled on a 5.0" Ø diameter bolt circle in the ring 150. For an oblique angle of 15° from normal impact (blast wave impacts the target face at 75°), the 5.0" Ø diameter target face bolt circle projects as a slight ellipse onto the ring 150. Numerical machining techniques were used to drill the three non-normal through-holes 175 in the appropriate position to align with the angled target assembly 630. Other orientations, i.e., 30°, can easily be selected by using the above numerical procedure.

The front plate 520 is fabricated from 0.25" thick 6061-T6 aluminum, has a 5.0" Ø o.d., 3.0" Ø i.d., and three ¼-28 threaded holes spaced 120° apart on a 4.5" Ø bolt circle. The obverse of the front plate 520 faces the shim 155. The reverse of the front plate 520 has an angular recess 525 for centering the target assembly that is 3.28" diameter by 0.15" thick. The obverse of the gauge assembly 410 fits into this recess 525. The recess 525 is 1.5" long, 25° off the center line, and 0.15" deep recess to prevent the stress gauge 470 in the proximal gauge package 420 from being damaged when the assembly 510 clamps together.

The rear plate 530 is fabricated from 0.5" thick polytetrafluoroethylene (PTFE), has a 5.75" Ø o.d., 2.75" Ø i.d., and three 0.28" Ø diameter straight through-holes 570 spaced 120° apart on a 5" bolt circle, as well as the three 0.028" Ø diameter straight through-holes 575 spaced 120° apart on a 4.5" Ø bolt circle offset 60° from the 570 hole pattern. The obverse of the back plate 530 has a recess (not shown, but similar to the recess 525) that is 3.28" Ø diameter by 0.04" deep for centering the target sample alignment.

The analysis process involves the calculation of the dynamic material parameters for the test sample 440 using the amplitude versus time data recorded by the stress gauges 480 and 485 in the exemplary target assembly 510. An impedance matching technique for waves is used to determine the speed of the acoustic wave in the layered panel and the amplitude of the input and output stress of the layered panel. The difference between the input and output stress of the panel is used to calculate blast attenuation.

First, the two gauge packages 420 and 450 are assembled. For each package, the stress sensor 470 as a gauge element is centered between the two 6061-T6 aluminum plates and epoxied in place using a low viscosity epoxy. Data wires are soldered onto the sensor leads. The test sample 440 is coated with a thin layer of vacuum grease to eliminate any interface voids between the sample 440 and aluminum of the gauge packages 420 and 450 that could disrupt blast wave transmission through them. The sample 440 is then sandwiched between the two gauge packages 420 and 450 for disposition in the mounting fixture 510. The rear plate 530 is tightened sufficiently against the gauge assembly 510 to maintain the sample 440 in position during testing.

The target assembly 510 is then attached to the flange 140 using three ¼-28 threaded rods 540. The spacing between the shim 155 of flange 140 and front plate 520 of the target assembly 510 is verified in three locations to ensure that the sample 440 is kept parallel to the flange 140. Data cables attached to the gauge leads are connected to two scopes that record the amplitude versus time data for each gauge sensor 480 and 485. This completes the normal test configuration 610. Similar arrangements operate for oblique test configuration 620.

The test event begins when the fast-acting valve in the gas gun is opened forming a planar blast wave 580 that travels down the 1.575" Ø bore diameter barrel until it reaches the muzzle adapter 120. A 5.75" long transition region 220 in the tube 130 causes the blast wave 580 to expand to 2.5" Ø diameter. This expansion of the blast wave 580 causes turbulence in the flow of the blast pressure.

The effect of this turbulence on the flow characteristics of the blast wave 580 depends on the magnitude of the blast pressure; i.e., the higher the pressure, the greater the effect. Therefore, the 2.5" Ø bore straight region 230 after the transition region 220 in the muzzle adapter 120 is 6.0" long to permit the turbulence to subside and the planar blast wave to reform prior to impact with the target assembly 610. The muzzle adapter 120 is equipped with a trigger sensor at the tap 160 to start the data acquisition system and two pressure gauges at taps 165 to record incident pressure and velocity of the blast wave prior to impact with the gauge assembly 410.

Figure 7:
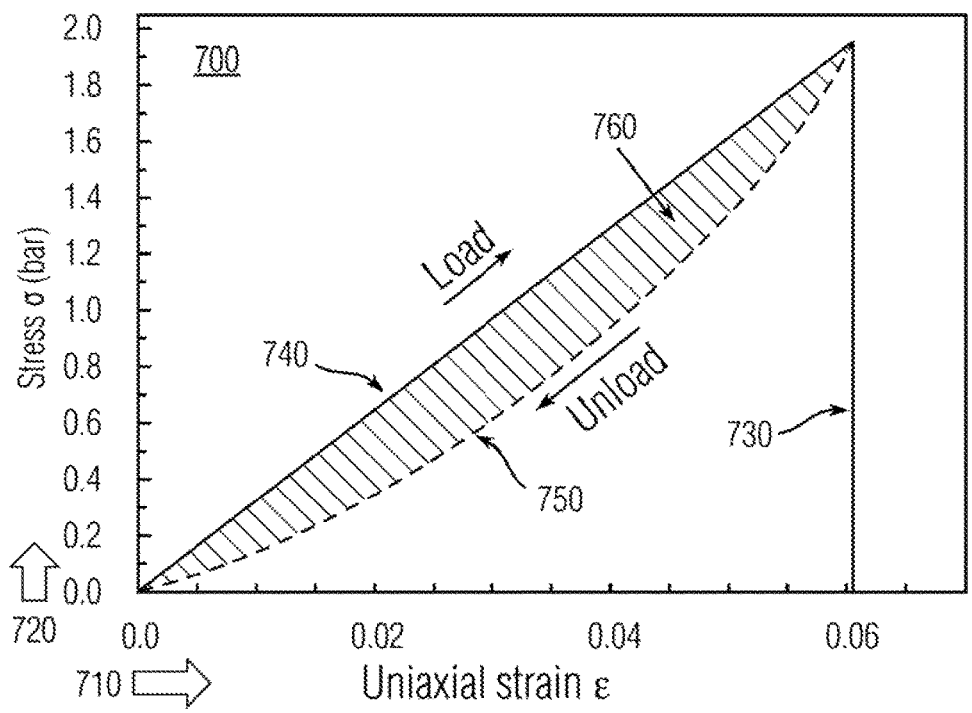
FIG. 7 is a graphical view of a stress-strain plot.

Calibration experiments for the 6061-T6 aluminum are conducted to determine the equation of state for aluminum. FIG. 7 shows a graphical view 700 of data collected from two stress gauges: PVDF1 480 and PVDF2 485 plotted as stress versus time plots to determine the blast wave time of arrival for each gauge and the interface stresses. The longitudinal wave velocity U is calculated according to the relation:

$$U = \frac{d}{(\Delta t - \Delta t_{Al} - \Delta t_G)}, \quad (1)$$

where d is the measured sample thickness, and Δt is the blast wave transit time that is taken as the time difference between the measured PVDF1 480 and PVDF2 485 signal responses.

Difference term $\Delta t_{Al}$ is the transit time through two 6061-T6 aluminum disks in a package 420 or 450 sandwiching one of the stress gauges 470, and is determined by dividing the thickness of the disks by the average measured longitudinal wave speed for the 6061-T6 aluminum calibration experiments. Difference term $\Delta t_G$ is the calculated transit time through the gauge sensor 480 or 485.

The particle velocity u is calculated according to the relation:

$$u = \frac{\sigma}{\rho_0 U}, \quad (2)$$

where σ is determined by impedance matching between the aluminum and sample, and $\rho_0$ is the density of the sample. The longitudinal wave velocity U can be plotted versus particle velocity u, with the addition of a linear least squares curve fit to provide an equation for longitudinal wave velocity in the form:

$$U = C_0 + su, \quad (3)$$

where $C_0$ is a velocity offset coefficient and s is an attenuation ratio.

A stress-strain relation can be plotted for the sample determined by $\sigma = \rho_0 U^2 \varepsilon$ where U is the linear least squares curve fit from the U–u plot. The curve is therefore of the form:

$$\sigma = \frac{\rho_0 C_0^2 \varepsilon}{(1 - s\varepsilon)^2}. \quad (4)$$

The stress σ is the interface stress between the first 6061-T6 aluminum disk 430 and the front of the sample 440 and is taken as the measured PVDF1 stress. The uniaxial engineering strain ε is the relation:

$$\varepsilon = \frac{u}{U}. \quad (5)$$

FIG. 7 shows a graphical view 700 of loading and unloading of a viscoelastic material. The abscissa 710 denotes uniaxial strain ε, while the ordinate 720 denotes stress σ in bars. A strain limit 730 identifies its maximum value. A load solid line 740 denotes linear strain rise with increasing stress. An unload dash line 750 denotes residual strain from decreasing stress.

A shaded area 760 between the lines 740 and 750 denotes absorption of deformation energy for calculating percent energy absorbed by the sample 440. As the sample 440 loads along the straight line load curve 740, some deformation energy is absorbed, and the sample 440 unloads along the stress-strain curve 750. The energy absorbed per unit volume denotes the area 760 between the loading and unloading curves.

Figure 8:
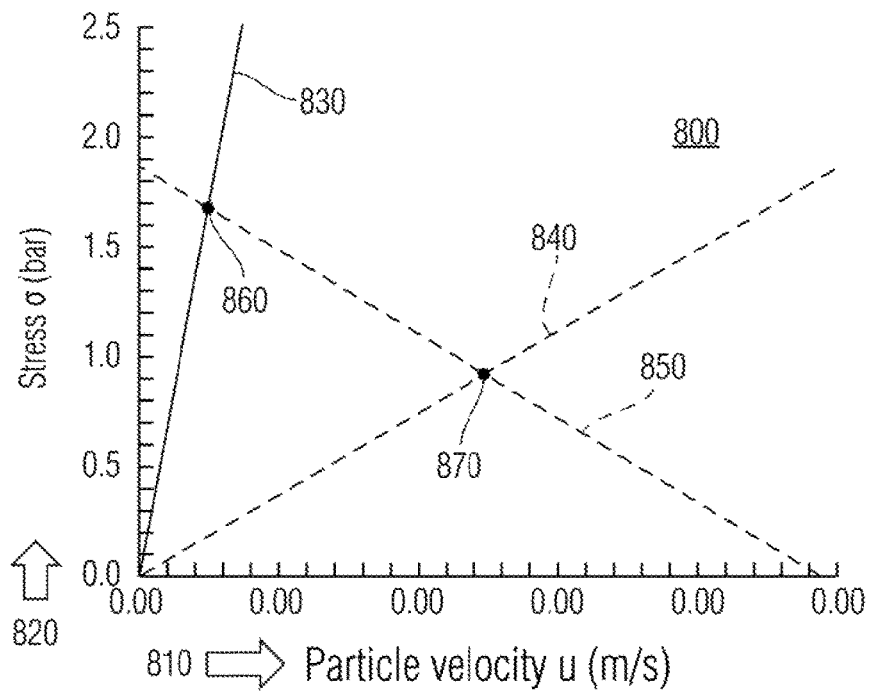
FIG. 8 is a graphical view of a stress-particle velocity plot.

To provide stress attenuation calculations, the stress at the aft surface of the sample 440 facing the disk 460 should be determined. This stress is less than the PVDF2 stress measurement. Thus, acoustic wave impedance matching techniques are used to formulate this calculation. Stress-particle velocity curves necessary for this determination are provided in FIG. 8 that shows a graphical view 800 of a sample plot procedure for a polymer sample. The abscissa 810 denotes particle velocity u in meters-per-second, while the ordinate 820 denotes stress σ in bars.

The depicted linear responses relating velocity to stress include a blast equation for positive-slope solid line 830, a polymer stress equation for positive-slope dash line 840 and a reflected polymer stress equation for negative-slope dash line 850. The intersection 860 between lines 830 and 850 identifies the stress measurement from PVDF2 485. The intersection 870 between lines 840 and 850 identifies polymer aft surface stress.

The reflected sample stress equation intersects the aluminum curve at the measured PVDF2 stress value. The 6061-T6 aluminum blast equation for line 830 can be expressed as:

$$\sigma = 172u, \quad (6)$$

based on calibration measurements. The polymer stress equation of measurements from PVDF1 480 for line 840 can be expressed as the curvefit:

$$\sigma = 18.4u + 3.9u^2. \quad (7)$$

The point where the reflected and non-reflected sample curves intersect is the back surface sample stress. This technique is used to determine the back surface sample stress for each experiment. Using these data and the measured PVDF1 values, one can determine blast attenuation values for the sample 440. Blast attenuation is calculated as the average percent reduction in the aft surface sample stress amplitude compared with the fore surface stress amplitude.

The graphical view 800 of the stress versus particle velocity plot is used for determining the aft surface sample stress. The percent blast attenuation can be expressed more fundamentally as an attenuation coefficient. An initial sound wave amplitude $A_0$ in a solid decreases exponentially to amplitude A after propagating a distance x according to:

$$A = A_0 \exp(-\alpha x), \qquad (8)$$

where α is the amplitude attenuation coefficient per unit distance. The coefficient α is determined by plotting 1 n($A/A_0$) versus polymer thickness x and calculating a linear least squares fit to all the data points.

While certain features of the embodiments of the invention have been illustrated as described herein, many modifications, substitutions, changes and equivalents will now occur to those skilled in the art. It is, therefore, to be understood that the appended claims are intended to cover all such modifications and changes as fall within the true spirit of the embodiments.

What is claimed is:

1. A test fixture for evaluating structural response of a sample to blast pressure from a muzzle of a gas gun, said fixture comprising:
   an adapter having a proximal rim and an expansion tube, said rim attaching to the muzzle to direct the blast pressure into said tube towards an exit opposite said rim;
   an annular flange having a ring and a shim that attaches to said tube at said exit;
   a gauge assembly that contains the sample between upstream and downstream stress gauges; and
   a target assembly that contains said gauge assembly, wherein
   said target assembly includes front and rear annular plates connecting coaxially in parallel,
   said rear annular plate connects to said ring, and
   said tube carries the blast pressure through said exit to strike said gauge assembly for said stress gauges to measure stress from the blast pressure.

2. The test fixture according to claim 1, wherein said gauge assembly includes fore and aft gauge packages for sandwiching the sample, said fore gauge package containing said upstream stress gauge and said aft gauge package containing said downstream stress gauge.

3. The test fixture according to claim 2, wherein each gauge package includes windward and leeward disks to sandwich a corresponding stress gauge.

4. The test fixture according to claim 3, wherein said disks are composed of 6061-T6 aluminum alloy, and each stress gauge is formed from polyvinylidene fluoride (PVDF).

5. The test fixture according to claim 1, wherein said ring includes first circumferentially distributed through-holes substantially parallel to said flange's symmetry axis and second circumferentially distributed mutually parallel through-holes angularly offset from said symmetry axis.

6. The test fixture according to claim 5, wherein said rear plate connects to said ring coaxially through said first through-holes by threaded rods secured by corresponding nuts.

7. The test fixture according to claim 5, wherein said rear plate connects to said ring obliquely through said second through-holes by threaded rods secured by corresponding nuts.

8. The test fixture according to claim 1, wherein said tube includes a tap for receiving a pressure gauge.

9. The test fixture according to claim 1, wherein said tube includes a plurality of taps disposed longitudinally for receiving pressure gauges.

10. The test fixture according to claim 1, wherein
    said tube at said exit includes bore holes parallel to a longitudinal axis of said tube,
    said shim includes through-holes that coaxially align with corresponding said bore holes such that each respective pair of holes receives a bolt to secure said flange to said adapter.

11. The test fixture according to claim 1, wherein said tube includes an upstream expansion segment and a downstream constant diameter segment.

12. The text fixture according to claim 1, wherein said adapter and annular flange are composed of 6061-T6 aluminum alloy and said rear annular plate is composed of polytetrafluoroethylene (PTFE).

* * * * *